(12) United States Patent
Mihori

(10) Patent No.: US 7,744,593 B2
(45) Date of Patent: Jun. 29, 2010

(54) HIGH-FREQUENCY POWER SUPPLY DEVICE AND ELECTROSURGICAL DEVICE

(75) Inventor: Takashi Mihori, Akiruno (JP)

(73) Assignee: Olympus Medical Systems Corp., Tokyo (JP)

( * ) Notice: Subject to any disclaimer, the term of this patent is extended or adjusted under 35 U.S.C. 154(b) by 846 days.

(21) Appl. No.: 11/593,299

(22) Filed: Nov. 6, 2006

(65) Prior Publication Data

US 2007/0123847 A1 May 31, 2007

(30) Foreign Application Priority Data

Nov. 28, 2005 (JP) .............................. 2005-342604

(51) Int. Cl.
*A61B 18/10* (2006.01)
*A61B 18/12* (2006.01)
(52) U.S. Cl. .............................. 606/38; 606/34; 606/37
(58) Field of Classification Search ................... 606/34, 606/38
See application file for complete search history.

(56) References Cited

U.S. PATENT DOCUMENTS

| 4,191,188 | A | * | 3/1980 | Belt et al. ...................... 606/37 |
| 5,372,596 | A | * | 12/1994 | Klicek et al. ................... 606/35 |
| 5,931,836 | A | * | 8/1999 | Hatta et al. ..................... 606/38 |
| 6,663,623 | B1 | * | 12/2003 | Oyama et al. .................. 606/38 |
| 6,663,836 | B1 | * | 12/2003 | Kalmakis et al. ............. 422/104 |
| 7,300,435 | B2 | * | 11/2007 | Wham et al. ................... 606/34 |
| 2004/0138654 | A1 | * | 7/2004 | Goble .......................... 606/34 |
| 2008/0103495 | A1 | * | 5/2008 | Mihori et al. ................. 606/38 |

FOREIGN PATENT DOCUMENTS

| JP | 8-507709 | 8/1996 |
| JP | 10-118093 | 5/1998 |
| JP | 2000-41994 | 2/2000 |
| JP | 2000-41995 | 2/2000 |
| JP | 2001-269353 | 10/2001 |
| JP | 2003-284725 | 10/2003 |

OTHER PUBLICATIONS

Abstract of WO 95/03743, dated Feb. 9, 1995.

* cited by examiner

*Primary Examiner*—Linda C Dvorak
*Assistant Examiner*—Jaymi Della
(74) *Attorney, Agent, or Firm*—Scully, Scott, Murphy & Presser, P.C.

(57) ABSTRACT

A high-frequency power supply device and an electrosurgical device are provided which can automatically control the output of an appropriate high-frequency current in accordance with the condition of a biological tissue to be treated. A phase detection unit detects respective phases of a high-frequency voltage and a high-frequency current outputted in a high-frequency power generation unit, and thereafter a phase difference calculation unit calculates the phase difference based on the respective phases. Meanwhile, an impedance calculation unit calculates the impedance on the basis of respective magnitudes of the high-frequency voltage and the high-frequency current. In this case, on the basis of at least one of the impedance and the phase difference and the output state of an instruction signal, a control unit performs a control to output a high-frequency voltage and a high-frequency current having a predetermined waveform. Accordingly, the output of the appropriate high-frequency current can be automatically controlled.

18 Claims, 4 Drawing Sheets

HIGH-FREQUENCY POWER SUPPLY DEVICE AND ELECTROSURGICAL DEVICE

The present application claims priority on the basis of Japanese Patent Application No. 2005-342604 filed in Japan on Nov. 28, 2005, and the following disclosed content is cited in the specification, the claims, and the drawings of the present application.

BACKGROUND OF THE INVENTION

1. Field of the Invention

The present invention relates to a high-frequency power supply device and an electrosurgical device capable of performing a treatment on a biological tissue with a high-frequency current.

2. Description of the Related Art

Conventionally, an electrosurgical device, such as an electric scalpel, has been used in a surgical operation or the like to perform such treatments as cutting, coagulation, and hemostasis of a biological tissue. Generally, the above-described electrosurgical device is configured to include a high-frequency power supply for outputting a high-frequency current, and a treatment tool connected to the high-frequency power supply. Through the treatment tool made in contact with a biological tissue of a patient, an operator or the like supplies the biological tissue with the high-frequency current outputted from the high-frequency power supply to thereby perform each of the above-described treatments on the biological tissue.

Further, it is desirable that the above-described electrosurgical device is configured to be able to supply the high-frequency current in accordance with the condition of the biological tissue to be treated or the treatment performed by the operator or the like. As a device approximately similar in configuration to the electrosurgical device having the above configuration, a high-frequency current curing device proposed in Japanese Unexamined Patent Application Publication No. 10-118093, for example, has been widely known.

SUMMARY OF THE INVENTION

A high-frequency power supply device according to the present invention is characterized by including: a high-frequency power generation unit for outputting a high-frequency voltage and supplying, via a treatment tool for performing a treatment on a biological tissue, a high-frequency current based on the high-frequency voltage to the biological tissue; a phase detection unit for detecting respective phases of the high-frequency voltage and the high-frequency current outputted from the high-frequency power generation unit; an impedance calculation unit for calculating the impedance of the biological tissue on the basis of the voltage magnitude of the high-frequency voltage outputted from the high-frequency power generation unit and the current magnitude of the high-frequency current outputted from the high-frequency power generation unit; a phase difference calculation unit for calculating the phase difference between the high-frequency voltage and the high-frequency current outputted from the high-frequency power generation unit on the basis of the respective phases detected by the phase detection unit; and a control unit for performing a control on the high-frequency power generation unit to output a high-frequency voltage and a high-frequency current having a predetermined waveform on the basis of at least one of the impedance and the phase difference and the output state of an instruction signal outputted from an operation instruction unit which can output the instruction signal for causing the high-frequency power supply device to supply the biological tissue with the high-frequency current.

DETAILED DESCRIPTION OF THE PREFERRED EMBODIMENTS

Figure 1:
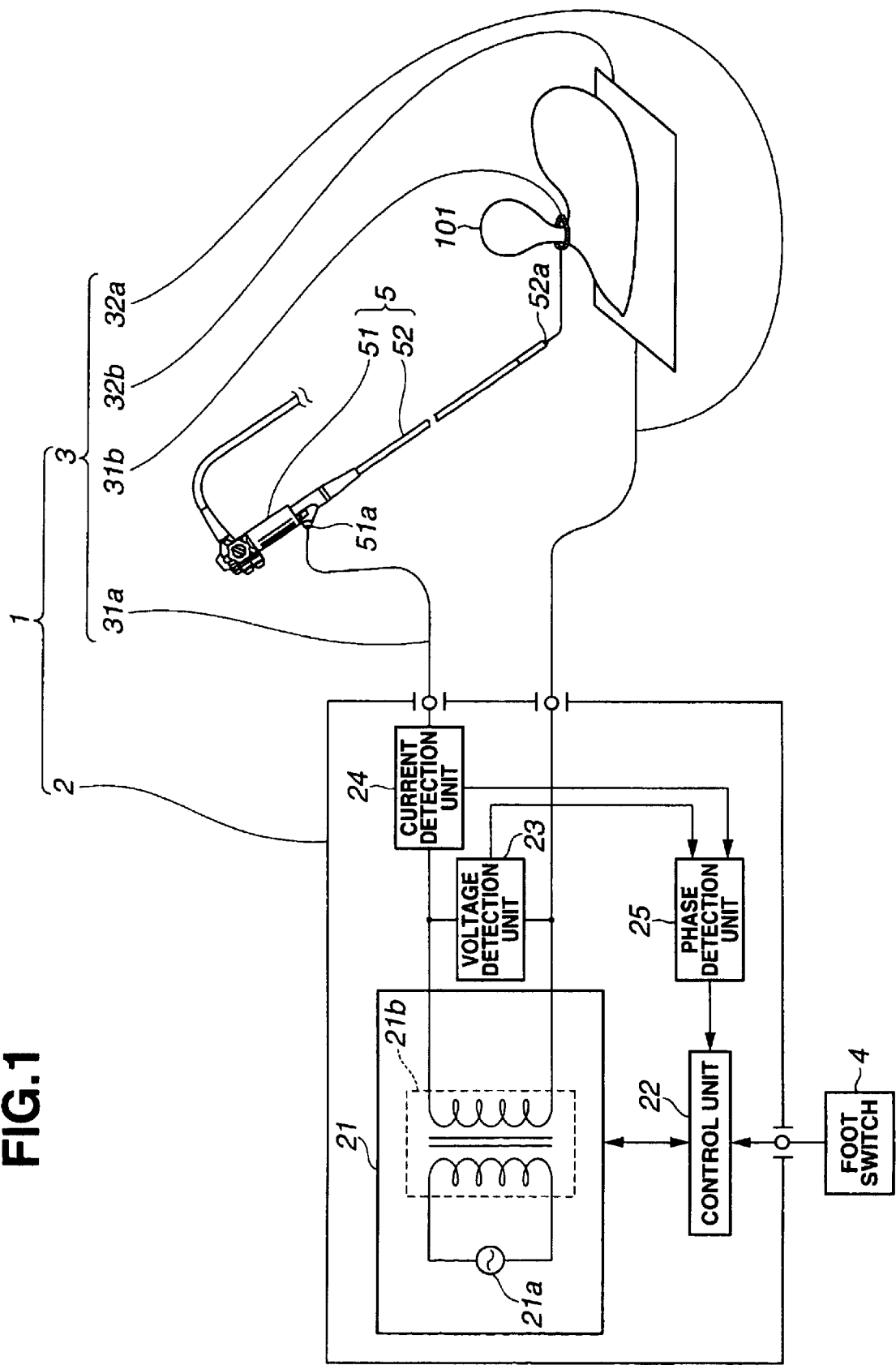
FIG. 1 is a diagram illustrating an example of a configuration of main parts in a case in which an electrosurgical device according to the present embodiment is used.
Figure 2:
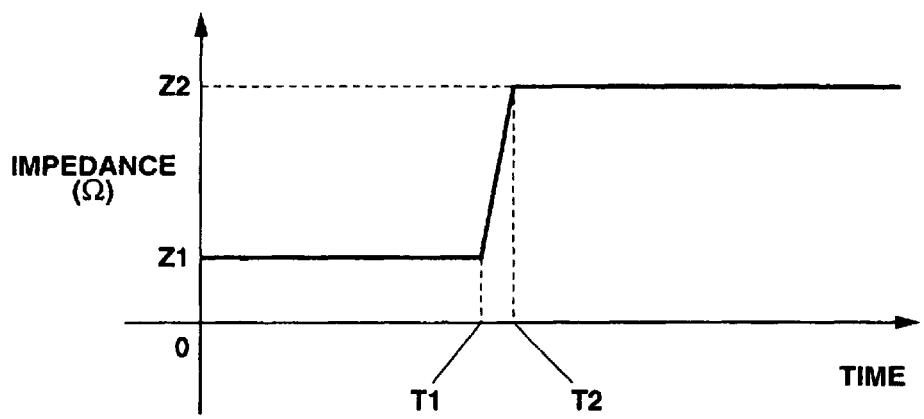
FIG. 2 is a diagram illustrating an example of a change over time of the impedance in a biological tissue in a case in which a high-frequency current is supplied to the biological tissue by the electrosurgical device illustrated in FIG. 1.
Figure 3:
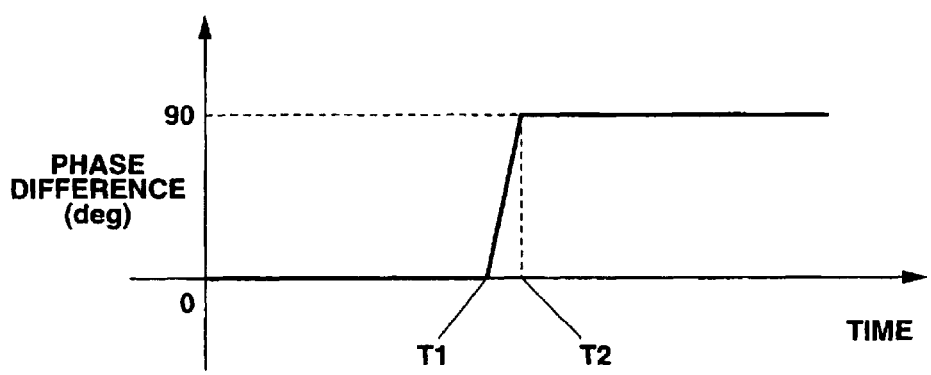
FIG. 3 is a diagram illustrating an example of a change over time of the phase difference between a high-frequency current and a high-frequency voltage outputted from the electrosurgical device in the case in which the high-frequency current is supplied to the biological tissue by the electrosurgical device illustrated in FIG. 1.
Figure 4:
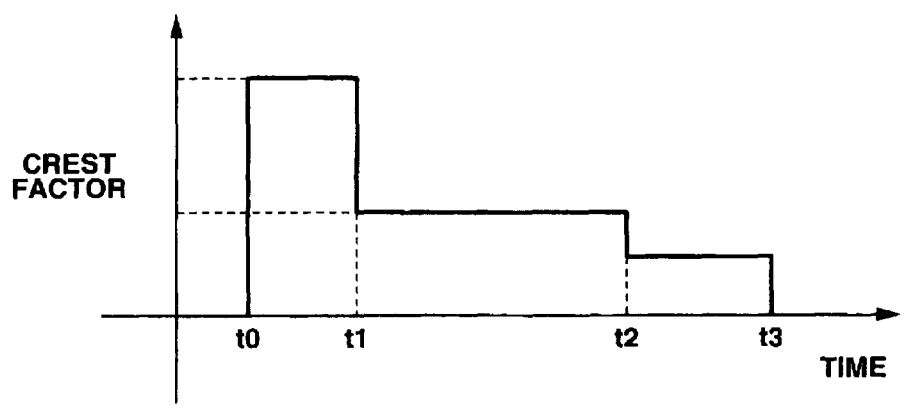
FIG. 4 is a diagram illustrating an example of a change over time of the crest factor of the high-frequency voltage outputted from the electrosurgical device illustrated in FIG. 1.
Figure 5:
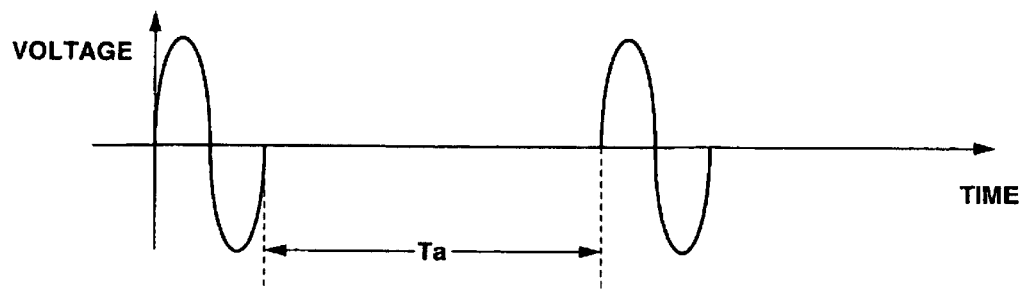
FIG. 5 is a diagram illustrating an example of a waveform of the high-frequency current supplied to the biological tissue by the electrosurgical device illustrated in FIG. 1.
Figure 6:
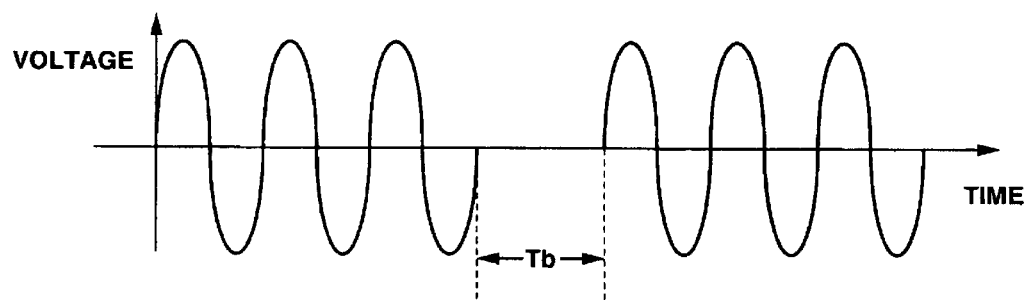
FIG. 6 is a diagram illustrating an example of the waveform of the high-frequency current supplied to the biological tissue by the electrosurgical device illustrated in FIG. 1, which is different from the example of FIG. 5.
Figure 7:
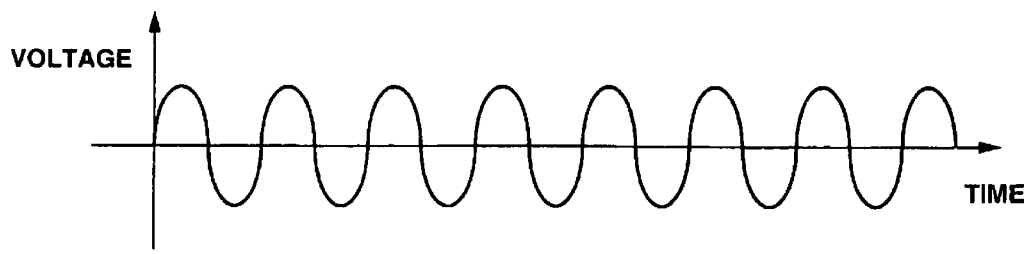
FIG. 7 is a diagram illustrating an example of the waveform of the high-frequency current supplied to the biological tissue by the electrosurgical device illustrated in FIG. 1, which is different from the examples of FIGS. 5 and 6.
Figure 8:
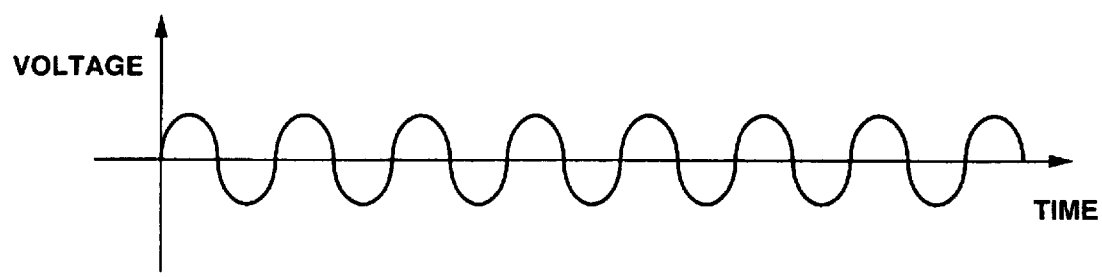
FIG. 8 is a diagram illustrating an example of the waveform of the high-frequency current supplied to the biological tissue by the electrosurgical device illustrated in FIG. 1, which is different from the examples of FIGS. 5, 6, and 7.

An embodiment of the present invention will be described below with reference to the drawings. FIG. 1 is a diagram illustrating an example of a configuration of main parts in a case in which an electrosurgical device according to the present embodiment is used. FIG. 2 is a diagram illustrating an example of a change over time of the impedance in a biological tissue in a case in which a high-frequency current is supplied to the biological tissue by the electrosurgical device illustrated in FIG. 1. FIG. 3 is a diagram illustrating an example of a change over time of the phase difference between a high-frequency current and a high-frequency voltage outputted from the electrosurgical device in the case in which the high-frequency current is supplied to the biological tissue by the electrosurgical device illustrated in FIG. 1. FIG. 4 is a diagram illustrating an example of a change over time of the crest factor of the high-frequency voltage outputted from the electrosurgical device illustrated in FIG. 1. FIG. 5 is a diagram illustrating an example of a waveform of the high-frequency current supplied to the biological tissue by the electrosurgical device illustrated in FIG. 1. FIG. 6 is a diagram illustrating an example of the waveform of the high-frequency current supplied to the biological tissue by the electrosurgical device illustrated in FIG. 1, which is different from the example of FIG. 5. FIG. 7 is a diagram illustrating an example of the waveform of the high-frequency current supplied to the biological tissue by the electrosurgical device illustrated in FIG. 1, which is different from the examples of FIGS. 5 and 6. FIG. 8 is a diagram illustrating an example of the waveform of the high-frequency current supplied to the biological tissue by the electrosurgical device illustrated in FIG. 1, which is different from the examples of FIGS. 5, 6, and 7.

As illustrated in FIG. 1, major parts of an electrosurgical device 1 include a high-frequency power supply device 2 which outputs a high-frequency current, and a monopolar-type treatment tool 3 which is connectable, at the basal end side thereof, to the high-frequency power supply device 2, and which supplies, from the distal end side thereof, the high-frequency current outputted from the high-frequency power supply device 2 to a biological tissue 101 to thereby perform a treatment on the biological tissue 101.

A foot switch 4 is connectable to the high-frequency power supply device 2 and is formed as an operation instruction unit for sending an instruction to the high-frequency power supply device 2. Specifically, the foot switch 4 is configured to output an instruction signal for causing high-frequency power supply device 2 to output the high-frequency current to the high-frequency power supply device 2 only during a period in which the foot switch 4 is pressed by an operator or the like, for example.

An endoscope 5 capable of capturing an image of a desired site of the biological tissue 101 includes an operation portion 51 held and operated by the operator or the like, and an insertion portion 52 having a size and shape enabling the insertion of the insertion portion 52 into a body cavity.

The operation portion 51 includes a treatment tool insertion port 51a which is formed as a part of the monopolar-type treatment tool 3 and into which a lead wire 31a and an active electrode 31b can be inserted. Further, the treatment tool insertion port 51a is formed in a coupled manner to a not-illustrated treatment tool insertion path through which the lead wire 31a and the active electrode 31b can be inserted and which passes through the operation portion 51 and the insertion portion 52.

The insertion part 52 is formed in a coupled manner, at the basal end side thereof, to the operation portion 51, and includes, at the distal end side thereof, an opening 52a formed in a coupled manner to the above-described, not-illustrated treatment tool insertion path.

Due to the above-described configuration of the endoscope 5, the lead wire 31a and the active electrode 31b inserted from the treatment tool insertion port 51a project from the opening 52a formed at the distal end side of the insertion portion 52 via the not-illustrated treatment tool insertion path.

The high-frequency power supply device 2 is configured to include a high-frequency power generation unit 21, a control unit 22, a voltage detection unit 23, a current detection unit 24, and a phase detection unit 25. Further, the high-frequency power generation unit 21 is configured to include an alternating power supply 21a for outputting an alternating voltage and an alternating current, and a high-frequency transformer 21b.

The alternating power supply 21a applies a high-frequency voltage having a peak value V1 and a frequency of approximately a few hundred kilohertz, for example, as a predetermined frequency to a primary circuit of the high-frequency transformer 21b.

When the high-frequency voltage having the predetermined frequency and the peak value V1 is applied to the primary circuit, the high-frequency transformer 21b causes a secondary circuit to generate a high-frequency voltage having the predetermined frequency and a peak value V2 through electromagnetic induction. Then, when the high-frequency voltage having the predetermined frequency and the peak value V2 is generated in the secondary circuit of the high-frequency transformer 21b, a high-frequency current based on the high-frequency voltage and having the predetermined frequency and a peak value I2 is outputted via the current detection unit 24 to the monopolar-type treatment tool 3 connected to the high-frequency power supply device 2.

The voltage detection unit 23 detects the peak value V2 of the high-frequency voltage generated in the secondary circuit of the high-frequency transformer 21b, and outputs the detected peak value V2 to the phase detection unit 25 as output voltage value information.

The current detection unit 24 detects the peak value I2 of the high-frequency current generated on the basis of the high-frequency voltage generated in the secondary circuit of the high-frequency transformer 21b, and outputs the detected peak value I2 to the phase detection unit 25 as output current value information.

The phase detection unit 25 detects the phase of the high-frequency voltage outputted from the high-frequency power generation unit 21 on the basis of the output voltage value information outputted from the voltage detection unit 23, and thereafter outputs the detected phase to the control unit 22 as output voltage phase information together with the output voltage value information. Further, the phase detection unit 25 detects the phase of the high-frequency current outputted from the high-frequency power generation unit 21 on the basis of the output current value information outputted from the current detection unit 24, and thereafter outputs the detected phase to the control unit 22 as output current phase information together with the output current value information.

On the basis of the output voltage value information, the output voltage phase information, the output current value information, and the output current phase information outputted from the phase detection unit 25, the control unit 22 formed by a CPU and the like calculates the value of an output impedance Zo as the impedance of the biological tissue 101, and also calculates a phase difference Δθ between the high-frequency voltage and the high-frequency current outputted from the high-frequency power generation unit 21. In other words, the control unit 22 is configured to have the function of an impedance calculation unit and the function of a phase difference calculation unit.

Then, on the basis of at least one of the values of the phase difference Δθ and the output impedance Zo and the pressed state of the foot switch 4, i.e., the output state of the instruction signal outputted from the foot switch 4, the control unit 22 performs a predetermined control on the high-frequency power generation unit 21 such that the output waveform of the high-frequency voltage generated in the secondary circuit of the high-frequency transformer 21b and the high-frequency current based on the high-frequency voltage has an appropriate crest factor. The details of the above predetermined control will be later described.

Further, on the basis of the instruction signal outputted in accordance with the operation of the foot switch 4 and at least one of the values of the phase difference Δθ and the output impedance Zo, the control unit 22 performs a control on the high-frequency power generation unit 21 to change the output state of the high-frequency current and the high-frequency voltage to be the ON state or the OFF state.

Furthermore, as well as the control on the high-frequency power generation unit 21, the control unit 22 performs a control on each of not-illustrated parts other than the high-frequency power generation unit 21 provided in the high-frequency power supply device 2.

The monopolar-type treatment tool 3 is configured to include the lead wire 31a, the active electrode 31b, a lead wire 32a, and a return electrode 32b configured to be sufficiently large in the contact area in contact with the biological tissue 101, as compared with the active electrode 31b.

The lead wire 31a is configured to be connectable, at the basal end side thereof, to the high-frequency power supply device 2, and to include, at the distal end side thereof, the active electrode 31b. With this configuration, the lead wire 31a can transmit the high-frequency current outputted from the high-frequency power supply device 2 to the active electrode 31b located at the distal end side.

Having been outputted from the high-frequency power supply device 2, the high-frequency current transmitted by the lead wire 31a is applied between the active electrode 31b formed as a high-frequency snare and the return electrode 32b formed as a counter electrode. Through the above-described operation, the high-frequency current outputted from the active electrode 31b is supplied to the biological tissue 101.

The lead wire 32a is configured to be connectable, at the basal end side thereof, to the high-frequency power supply device 2, and to include, at the distal end side thereof, the return electrode 32b. With this configuration, the lead wire 32a can return the high-frequency current supplied to the biological tissue 101 to the high-frequency power supply device 2.

The operation of the electrosurgical device 1 will be then described.

The operator or the like first connects the lead wires 31a and 32a of the monopolar-type treatment tool 3 to the high-frequency power supply device 2. Then, to perform the treatment using the monopolar-type treatment tool 3 while watching the image of the biological tissue 101 captured by the endoscope 5 on a not-illustrated monitor or the like, the operator or the like operates the endoscope 5 to direct the opening 52a of the insertion portion 52 to the desired site of the biological tissue 101.

Further, the operator or the like inserts, from the treatment tool insertion port 51a, the lead wire 31a and the active electrode 31b of the monopolar-type treatment tool 3 connected to the high-frequency power supply device 2, to make the lead wire 31a and the active electrode 31b inserted through the not-illustrated treatment tool insertion path inside the endoscope 5 and projected from the opening 52a. Furthermore, the operator or the like locates the active electrode 31b and the return electrode 32b at positions in the biological tissue 101 at which the two electrodes are approximately opposite to each other so as to sandwich the desired site as the site to be treated with the high-frequency current.

Then, when the foot switch 4 is pressed by the operator or the like in the above-described state, the instruction signal, which includes the instruction to supply the high-frequency current to the site to be treated and targeted of the biological tissue 101, is outputted from the foot switch 4 to the control unit 22.

Meanwhile, as illustrated in FIG. 2, the impedance of the biological tissue 101 is relatively low due to the adhesion of mucus or the like in an early stage of the treatment on the biological tissue 101. Further, as illustrated in FIG. 3, the phase difference between the high-frequency current and the high-frequency voltage outputted from the high-frequency power supply device 2 is 0° C. or approximately 0° C. in the early stage of the treatment on the biological tissue 101, since components of the impedance of the biological tissue 101 are substantially dominated by a pure resistance component.

Therefore, on the basis of the output voltage value information, the output voltage phase information, the output current value information, and the output current phase information outputted from the phase detection unit 25 in the early stage of the treatment on the biological tissue 101, the control unit 22 calculates the value of the output impedance Zo, and also calculates the phase difference $\Delta\theta$ between the high-frequency voltage and the high-frequency current outputted from the high-frequency power generation unit 21. Then, on the basis of at least one of the values of the phase difference $\Delta\theta$ and the output impedance Zo and the instruction signal outputted in accordance with the operation of the foot switch 4, the control unit 22 performs a control on the high-frequency power generation unit 21 to change the output state of the high-frequency current and the high-frequency voltage to be the ON state. Specifically, if the output impedance Zo has been calculated to be Z1 as indicated in FIG. 2, and if the phase difference $\Delta\theta$ has been calculated to be 0° as indicated in FIG. 3, for example, the control unit 22 performs a control on the high-frequency power generation unit 21 to output a high-frequency voltage and a high-frequency current having a waveform with a high crest factor, as illustrated in FIG. 4, on the basis of the above calculation results and the above instruction signal outputted at a time t0 which is a time immediately after the pressing of the foot switch 4.

On the basis of the control by the control unit 22, the high-frequency power generation unit 21 causes the secondary circuit of the high-frequency transformer 21b to generate the high-frequency voltage having the waveform with a high crest factor. Specifically, the waveform with a high crest factor includes, for example, a coagulation waveform as illustrated in FIG. 5, which is a sine wave of one period repeatedly outputted after the elapse of a first predetermined time interval Ta, and a mixed waveform as illustrated in FIG. 6, which is a sine wave of a predetermined number of periods repeatedly outputted after the elapse of a second predetermined time interval Tb.

Then, if the high-frequency voltage having the waveform with a high crest factor is generated in the secondary circuit of the high-frequency transformer 21b, the high-frequency current based on the high-frequency voltage and having the waveform with a high crest factor is supplied, via the current detection unit 24 and the lead wire 31a of the monopolar-type treatment tool 3, to the desired site of the biological tissue 101 sandwiched by the active electrode 31b and the return electrode 32b.

According to the above-described operation, the desired site of the biological tissue 101 as the site to be treated with the high-frequency current is supplied with the high-frequency current having the waveform with a high crest factor in the early stage of the treatment. Therefore, the desired site including blood vessels running under the tissue is surely coagulated.

Thereafter, if the treatment at the desired site proceeds as the foot switch 4 continues to be pressed, the output impedance Zo increases from a time T1 at which the adhered mucus or the like has been substantially completely dehydrated, as illustrated in FIG. 2. Further, if the treatment at the desired site proceeds as the foot switch 4 continues to be pressed, the phase difference $\Delta\theta$ between the high-frequency voltage and the high-frequency current outputted from the high-frequency power generation unit 21 increases from 0° or approximately 0° from the time T1 at which the adhered mucus or the like has been substantially completely dehydrated, as illustrated in FIG. 3.

Therefore, on the basis of the output voltage value information, the output voltage phase information, the output current value information, and the output current phase information outputted from the phase detection unit 25, the control unit 22 calculates the value of the output impedance Zo and the phase difference Δθ. Further, as illustrated in FIG. 4, on the basis of the above calculation results, the control unit 22 performs a control on the high-frequency power generation unit 21 to output a high-frequency voltage and a high-frequency current having a waveform with a low crest factor at a time t1 which has the relationship T1≦t1.

In other words, if the foot switch 4 continues to be pressed, and upon detection of the increase of the phase difference Δθ from 0° or approximately 0°, the control unit 22 performs a control on the high-frequency power generation unit 21 to output a high-frequency voltage and a high-frequency current having a waveform with a lower crest factor than that of the waveform obtained prior to the time t1.

In still other words, if the foot switch 4 continues to be pressed, and upon detection of the increase of the output impedance Zo from Z1 as indicated in FIG. 2, the control unit 22 performs the control on the high-frequency power generation unit 21 to output the high-frequency voltage and the high-frequency current having the waveform with the lower crest factor than that of the waveform obtained prior to the time t1.

On the basis of the control by the control unit 22, the high-frequency power generation unit 21 causes the secondary circuit of the high-frequency transformer 21b to generate the high-frequency voltage having the waveform with a low crest factor. Specifically, the waveform with a low crest factor includes, for example, a cutting waveform as illustrated in FIG. 7, which is a continuously outputted sine wave.

Then, if the high-frequency voltage having the waveform with the lower crest factor than that of the waveform obtained prior to the time t1 is generated in the secondary circuit of the high-frequency transformer 21b, a high-frequency current based on the high-frequency voltage and having the waveform with a low crest factor is supplied, via the current detection unit 24 and the lead wire 31a of the monopolar-type treatment tool 3, to the desired site of the biological tissue 101 sandwiched by the active electrode 31b and the return electrode 32b.

According to the above-described operation, the desired site of the biological tissue 101 as the site to be treated with the high-frequency current is supplied with the high-frequency current having the waveform with a low crest factor in a stage after the elapse of a predetermined time since the start of the treatment. Therefore, the desired site including blood vessels running under the tissue is cut in the state in which the site has been surely coagulated.

Thereafter, if the treatment at the desired site proceeds as the foot switch 4 further continues to be pressed, the value of the output impedance Zo calculated by the control unit 22 becomes a constant value indicated as Z2 in FIG. 2 in the state in which the adhered mucus or the like has been completely dehydrated, i.e., at and after a time T2 which has the relationship T1≦t1<T2. Further, at and after the time T2, the value of the phase difference Δθ calculated by the control unit 22 becomes a constant value around 90° as indicated in FIG. 3.

Therefore, on the basis of the output voltage value information, the output voltage phase information, the output current value information, and the output current phase information outputted from the phase detection unit 25, the control unit 22 calculates the value of the output impedance Zo and the phase difference Δθ. Then, as illustrated in FIG. 4, on the basis of the above calculation results, the control unit 22 performs a control on the high-frequency power generation unit 21 to decrease the crest factor by decreasing the peak value V2 of the outputted high-frequency voltage at the time t2 which has the relationship T2≦t2 and by which at least one of the values of the output impedance Zo and the phase difference Δθ has become constant.

In other words, if the foot switch 4 further continues to be pressed after the time t1, and upon detection that the phase difference Δθ has increased from 0° or approximately 0° to a constant value around 90° as indicated in FIG. 3, the control unit 22 performs a control on the high-frequency power generation unit 21 to output a high-frequency voltage and a high-frequency current having a waveform with a lower crest factor than that of the waveform obtained prior to the time t2.

In the present embodiment, the control unit 22 is not limited to the one which performs the above-described control upon detection that the phase difference Δθ has become the constant value around 90°. Thus, for example, the control unit 22 may perform the above-described control upon detection that the phase difference Δθ has become constant at a predetermined value greater than 45° and equal to or smaller than 90°.

In still other words, if the foot switch 4 further continues to be pressed after the time t1, and upon detection that the output impedance Zo has increased from Z1 to Z2 and has become constant, the control unit 22 performs the control on the high-frequency power generation unit 21 to output the high-frequency voltage and the high-frequency current having the waveform with the lower crest factor than that of the waveform obtained prior to the time t2, as indicated in FIG. 4.

On the basis of the control by the control unit 22, the high-frequency power generation unit 21 decreases the peak value V2 of the high-frequency voltage outputted in the secondary circuit of the high-frequency transformer 21b to an approximately minimum value required to cut the biological tissue 101 to thereby generate a high-frequency voltage having a waveform as illustrated in FIG. 8 with a further lower crest factor than that of the high-frequency voltage outputted prior to the time t2. The waveforms as illustrated in FIGS. 5 to 8 are drawn to the same scale.

If the high-frequency voltage having the waveform with the further lower crest factor than that of the high-frequency voltage outputted prior to the time t2 is generated in the secondary circuit of the high-frequency transformer 21b, a high-frequency current based on the high-frequency voltage and having the waveform with the further lower crest factor than that of the high-frequency current outputted prior to the time t2 is supplied, via the current detection unit 24 and the lead wire 31a of the monopolar-type treatment tool 3, to the desired site of the biological tissue 101 sandwiched by the active electrode 31b and the return electrode 32b.

The high-frequency current continues to be outputted from the high-frequency power generation unit 21 during a period until a time t3 as indicated in FIG. 4, which has the relationship t2≦t3 and at which the output of the instruction signal from the foot switch 4 is stopped as the pressed state of the foot switch 4 is released. Then, upon detection of the stop of the instruction signal outputted from the foot switch 4, the control unit 22 performs a control on the high-frequency power generation unit 21 to change the output state of the high-frequency current and the high-frequency voltage to be the OFF state.

According to the above-described operation, the desired site of the biological tissue 101 as the site to be treated with the high-frequency current is supplied with the high-frequency current having the approximately minimal peak value required to cut the desired site in a stage in which a sufficient time for completely dehydrating the desired site has elapsed since the start of the treatment. Therefore, the desired site is cut without being excessively damaged.

As described above, according to the high-frequency power supply device 2 and the electrosurgical device 1 of the present embodiment, in the early stage of the treatment on the site of the biological tissue 101 to be treated with the high-frequency current, the site is supplied with the high-frequency current having the waveform with a high crest factor, i.e., the high-frequency current having a low resection effect and a high hemostasis effect. Thereby, in the early stage of the treatment, the site is dehydrated and coagulated in a short time period without being insufficiently burned or bleeding. Accordingly, the high-frequency power supply device 2 and the electrosurgical device 1 of the present embodiment can prevent the decrease of the effect of the treatment performed by the operator or the like on the biological tissue by using the high-frequency current, and also can reduce the time spent for the treatment.

Further, according to the high-frequency power supply device 2 and the electrosurgical device 1 of the present embodiment, the above-described controls are performed by the control unit 22. It is therefore possible to automatically control the output of the appropriate high-frequency current in accordance with the condition of the biological tissue to be treated.

Needless to say, the present invention is not limited to the embodiment described above, but various modifications and applications can be made in the present invention within a scope not departing from the gist of the invention.

What is claimed is:

1. A high-frequency power supply device comprising:
   a high-frequency power generation unit for outputting a high-frequency voltage and supplying, via a treatment tool for performing a treatment on a biological tissue, a high-frequency current based on the high-frequency voltage to the biological tissue;
   a phase detection unit for detecting respective phases of the high-frequency voltage and the high-frequency current outputted from the high-frequency power generation unit;
   an impedance calculation unit for calculating the impedance of the biological tissue on the basis of the voltage magnitude of the high-frequency voltage outputted from the high-frequency power generation unit and the current magnitude of the high-frequency current outputted from the high-frequency power generation unit;
   a phase difference calculation unit for calculating the phase difference between the high-frequency voltage and the high-frequency current outputted from the high-frequency power generation unit on the basis of the respective phases detected by the phase detection unit; and
   a control unit for performing a control on the high-frequency power generation unit to output a high-frequency voltage and a high-frequency current having a predetermined waveform on the basis of at least one of the impedance and the phase difference and the output state of an instruction signal outputted from an operation instruction unit which can output the instruction signal for causing the high-frequency power supply device to supply the biological tissue with the high-frequency current, wherein
   immediately after the output of the instruction signal, the control unit further performs a first control on the high-frequency power generation unit to output a high-frequency voltage and a high-frequency current having a first waveform, and when the instruction signal continues to be outputted, and upon detection that the phase difference has increased from 0°, the control unit further performs, subsequent to the first control, a second control on the high-frequency power generation unit to output a high-frequency voltage and a high-frequency current having a second waveform with a lower crest factor than that of the first waveform.

2. The high-frequency power supply device according to claim 1, wherein, when the instruction signal continues to be outputted, and upon detection that the phase difference has increased from 0° and has become constant at a predetermined value, the control unit further performs, subsequent to the second control, a third control on the high-frequency power generation unit to output a high-frequency voltage and a high-frequency current having a third waveform with a lower crest factor than that of the second waveform.

3. The high-frequency power supply device according to claim 2, wherein the predetermined value is greater than 45° and equal to or smaller than 90°.

4. The high-frequency power supply device according to claim 1, wherein the first waveform is a sine wave of a predetermined number of periods repeatedly outputted after the elapse of a predetermined time interval.

5. The high-frequency power supply device according to claim 2, wherein the first waveform is a sine wave of a predetermined number of periods repeatedly outputted after the elapse of a predetermined time interval.

6. The high-frequency power supply device according to claim 3, wherein the first waveform is a sine wave of a predetermined number of periods repeatedly outputted after the elapse of a predetermined time interval.

7. The high-frequency power supply device according to claim 1, wherein the second waveform is a continuously outputted sine wave.

8. The high-frequency power supply device according to claim 2, wherein the second waveform is a continuously outputted sine wave.

9. The high-frequency power supply device according to claim 3, wherein the second waveform is a continuously outputted sine wave.

10. An electrosurgical device comprising:
    a treatment tool for performing a treatment on a biological tissue; and
    a high-frequency power supply device which outputs a high-frequency voltage on the basis of an instruction signal outputted from an operation instruction unit capable of outputting the instruction signal for causing the output of a high-frequency current to the biological tissue, and which outputs the high-frequency current based on the high-frequency voltage via the treatment tool,
    the electrosurgical device further comprising:
    a phase detection unit for detecting respective phases of the high-frequency voltage and the high-frequency current outputted from the high-frequency power supply device;
    an impedance calculation unit for calculating the impedance of the biological tissue on the basis of the voltage magnitude of the high-frequency voltage outputted from the high-frequency power supply device and the current magnitude of the high-frequency current outputted from the high-frequency power supply device;
    a phase difference calculation unit for calculating the phase difference between the high-frequency voltage and the high-frequency current outputted from the high-frequency power supply device on the basis of the respective phases detected by the phase detection unit; and
    a control unit for performing a control on the high-frequency power supply device to output a high-frequency voltage and a high-frequency current having a predetermined waveform on the basis of at least one of the impedance and the phase difference and the output state of the instruction signal, wherein
immediately after the output of the instruction signal, the control unit further performs a first control on the high-frequency power supply device to output a high-frequency voltage and a high-frequency current having a first waveform, and when the instruction signal continues to be outputted, and upon detection that the phase difference has increased from 0°, the control unit further performs, subsequent to the first control, a second control on the high-frequency power supply device to output a high-frequency voltage and a high-frequency current having a second waveform with a lower crest factor than that of the first waveform.

11. The electrosurgical device according to claim 10, wherein, when the instruction signal continues to be outputted, and upon detection that the phase difference has increased from 0° and has become constant at a predetermined value, the control unit further performs, subsequent to the second control, a third control on the high-frequency power supply device to output a high-frequency voltage and a high-frequency current having a third waveform with a lower crest factor than that of the second waveform.

12. The electrosurgical device according to claim 11, wherein the predetermined value is greater than 45° and equal to or smaller than 90°.

13. The electrosurgical device according to claim 10, wherein the first waveform is a sine wave of a predetermined number of periods repeatedly outputted after the elapse of a predetermined time interval.

14. The electrosurgical device according to claim 11, wherein the first waveform is a sine wave of a predetermined number of periods repeatedly outputted after the elapse of a predetermined time interval.

15. The electrosurgical device according to claim 12, wherein the first waveform is a sine wave of a predetermined number of periods repeatedly outputted after the elapse of a predetermined time interval.

16. The electrosurgical device according to claim 10, wherein the second waveform is a continuously outputted sine wave.

17. The electrosurgical device according to claim 11, wherein the second waveform is a continuously outputted sine wave.

18. The electrosurgical device according to claim 12, wherein the second waveform is a continuously outputted sine wave.

* * * * *